United States Patent
Root et al.

(10) Patent No.: US 7,985,500 B2
(45) Date of Patent: Jul. 26, 2011

(54) METHOD AND APPARATUS FOR FLEXIBLE BATTERY FOR IMPLANTABLE DEVICE

(75) Inventors: Michael J. Root, Lino Lakes, MN (US); Nick A. Youker, River Falls, WI (US)

(73) Assignee: Cardiac Pacemakers, Inc., St. Paul, MN (US)

(*) Notice: Subject to any disclaimer, the term of this patent is extended or adjusted under 35 U.S.C. 154(b) by 750 days.

(21) Appl. No.: 11/611,649

(22) Filed: Dec. 15, 2006

(65) Prior Publication Data
US 2007/0156184 A1 Jul. 5, 2007

Related U.S. Application Data

(60) Provisional application No. 60/750,531, filed on Dec. 15, 2005.

(51) Int. Cl.
*H01M 6/46* (2006.01)
*A61N 5/06* (2006.01)

(52) U.S. Cl. .......................... 429/162; 607/88

(58) Field of Classification Search .............. 607/88, 607/92; 600/508; 429/162
See application file for complete search history.

(56) References Cited

U.S. PATENT DOCUMENTS

| | | | |
|---|---|---|---|
| 4,092,464 A | 5/1978 | Dey et al. | |
| 5,511,553 A * | 4/1996 | Segalowitz | 600/508 |
| 5,580,676 A | 12/1996 | Honda et al. | |
| 5,645,586 A | 7/1997 | Meltzer | |
| RE35,746 E | 3/1998 | Lake et al. | |
| 5,776,169 A | 7/1998 | Schroeppel | |
| 5,935,154 A | 8/1999 | Westlund | |
| 6,272,379 B1 | 8/2001 | Fischell et al. | |
| 6,273,904 B1 * | 8/2001 | Chen et al. | 607/88 |
| 6,445,948 B1 | 9/2002 | Somdahl et al. | |
| 6,498,951 B1 | 12/2002 | Larson et al. | |
| 6,514,276 B2 | 2/2003 | Munshi | |
| 6,528,204 B1 | 3/2003 | Hikmet et al. | |
| 6,664,335 B2 | 12/2003 | Krishnan | |
| 6,665,191 B2 | 12/2003 | Blood et al. | |

(Continued)

FOREIGN PATENT DOCUMENTS

| WO | WO-94/15371 A1 | 7/1994 |
|---|---|---|
| WO | WO-98/37926 A1 | 9/1998 |
| WO | WO-2007/070717 A2 | 6/2007 |

OTHER PUBLICATIONS

"International Application Serial No. PCT/US2006/048125, International Search Report mailed Aug. 21, 2007", 4 pgs.

(Continued)

*Primary Examiner* — Carl H. Layno
*Assistant Examiner* — Jon-Eric C. Morales
(74) *Attorney, Agent, or Firm* — Schwegman, Lundberg & Woessner, P.A.

(57) ABSTRACT

One embodiment of the present subject matter includes an apparatus for storing energy, the apparatus having a first portion comprising a flexible substrate containing a polymer electrolyte and a second portion adapted to provide a conformable housing surrounding the first portion; wherein the apparatus is adapted to provide a source of energy to an implantable device. The apparatus defines a flexible implantable device capable of traversing the circulatory system of a body with minimal obstruction of flow within the circulatory system. Further provided is a method of implanting an power source within the circulatory system of a subject's body.

22 Claims, 1 Drawing Sheet

U.S. PATENT DOCUMENTS

| | | | |
|---|---|---|---|
| 6,676,714 B2 | 1/2004 | Langan | |
| 6,961,619 B2 | 11/2005 | Casey | |
| 7,013,739 B2 | 3/2006 | Schroeder et al. | |
| 7,070,881 B2 | 7/2006 | Kishiyama et al. | |
| 7,120,495 B2 | 10/2006 | Bardy | |
| 7,120,496 B2 | 10/2006 | Bardy et al. | |
| 7,479,349 B2 | 1/2009 | O'Phelan et al. | |
| 2002/0000034 A1* | 1/2002 | Jenson | 29/623.5 |
| 2002/0004167 A1* | 1/2002 | Jenson et al. | 429/162 |
| 2002/0065373 A1* | 5/2002 | Krishnan | 525/455 |
| 2002/0193844 A1 | 12/2002 | Michelson et al. | |
| 2003/0149459 A1 | 8/2003 | Von Arx et al. | |
| 2004/0127952 A1 | 7/2004 | O'Phelan et al. | |
| 2005/0189139 A1 | 9/2005 | Scott | |
| 2006/0211936 A1 | 9/2006 | Hu et al. | |
| 2007/0099071 A1 | 3/2007 | Morgan et al. | |
| 2007/0092794 A1 | 4/2007 | Coffey et al. | |
| 2007/0156197 A1 | 7/2007 | Root et al. | |
| 2009/0280153 A1* | 11/2009 | Hunter et al. | 424/423 |

OTHER PUBLICATIONS

"International Application Serial No. PCT/US2006/048125, Written Opinion mailed Aug. 21, 2007", 6 pgs.

"U.S. Appl. No. 11/611,658, response filed Dec. 28, 2009 to Restriction Requirement mailed Oct. 1, 2009", 6 pgs.

"U.S. Appl. No. 11/611,658, Restriction Requirement mailed Oct. 1, 2009", 6 pgs.

"European Application Serial No. 06847702.5, Office Action mailed Apr. 21, 2009", 2 pgs.

"U.S. Appl. No. 11/611,658, Non-Final Office Action mailed Mar. 19, 2010", 11 pgs.

"U.S. Appl. No. 11/611,658, Final Office Action mailed Nov. 17, 2010", 7 pgs.

"U.S. Appl. No. 11/611,658, Response filed Sep. 16, 2010 to Non-Final Office Action mailed Mar. 19, 2010", 14 pgs.

"European Application Serial No. 06847702.5, Response filed Oct. 30, 2009 to Office Action mailed Apr. 21, 2009", 20 pgs.

* cited by examiner

METHOD AND APPARATUS FOR FLEXIBLE BATTERY FOR IMPLANTABLE DEVICE

CROSS-REFERENCE TO RELATED APPLICATIONS

This application claims the benefit under 35 U.S.C. 119(e) of U.S. Provisional Patent Application Ser. No. 60/750,531, filed Dec. 15, 2005, the entire disclosure of which is hereby incorporated by reference in its entirety.

The following commonly assigned U.S. patent applications are related and are all incorporated by reference in their entirety: "Batteries Including a Flat Plate Design," U.S. Patent Publication No. 2004/0127952, filed Feb. 7, 2003; "Batteries Including a Flat Plate Design," U.S. Provisional Application Ser. No. 60/437,537 filed Dec. 31, 2002; "System and Method for Sealing Battery Separator," Ser. No. 11/264, 996, filed Nov. 2, 2005; "Polyurethane Elastomer Article with 'Shape Memory' and Medical Devices Therefrom," U.S. Pat. No. 6,664,335, filed Nov. 30, 2000; "Method and Apparatus for Improved Battery Profile," U.S. Provisional Application Ser. No. 60/750,517, filed Dec. 15, 2005.

TECHNICAL FIELD

This disclosure relates generally to an apparatus and method for power sources for use with an implantable device.

BACKGROUND

Self-powered devices are size-limited in part by the size of a power source used to power the device. Additionally, the shape of the power source impacts the size of the self-powered device. As such, existing power sources limit the range of shapes a self-powered device may take.

This is important in the area of implantable devices. Implantable devices, such as implantable medical devices, are increasingly able to perform new functions. However, the range of possible functions is limited by power source size and/or shape. For example, anatomical obstacles, such as the size of vessels of the circulatory system, limit the applicability of existing medical devices using known power sources. These existing medical devices are larger than preferred for implantation in some portions of the circulatory system. As such, there is a need in the art for improved flexibility in power source size and/or shape. Further, safety, patient comfort, device mass, service duration, and other factors require ongoing improvements in power sources for self-powered devices.

SUMMARY

The above-mentioned problems and others not expressly discussed herein are addressed by the present subject matter and will be understood by reading and studying this specification.

One embodiment of the present subject matter includes an apparatus for storing energy, the apparatus having a first portion comprising a flexible substrate containing a polymer electrolyte and a second portion adapted to provide a conformable housing surrounding the first portion; wherein the apparatus is adapted to provide a source of energy to an implantable device. The apparatus defines a flexible implantable device capable of traversing the circulatory system of a body with minimal obstruction of flow within the circulatory system.

An additional embodiment of the present subject matter includes an apparatus having one or more single cells contained within a flexible housing; wherein the apparatus is adaptable to provide a source of energy to an implantable device.

In some embodiments, the apparatus includes both a sensor and a power source contained within a flexible housing. In other embodiments, the housing includes an anchoring mechanism for anchoring the device during implantation within the body.

An additional embodiment of the present subject matter includes a series of smaller battery cells attached by flexible conductive interconnects that are further contained within a conformable housing capable of traversing the circulatory system of a body.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

Figure 1:
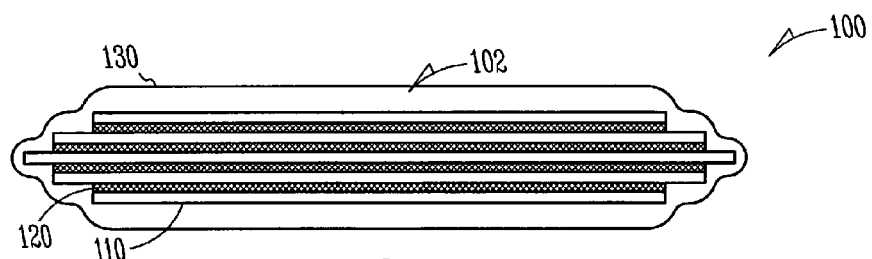
FIG. 1 is a cross section of an implantable device including a plurality of flexible battery layers, according to one embodiment of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Various embodiments of the present subject matter include implantable devices. Implantable devices contemplated by the present subject matter include, but are not limited to, self-powered implantable sensors. Self-powered implantable sensors, in various embodiments, provide a wireless signal which can be read by one or more receivers. Some embodiments of the present subject matter include receivers which are located in the patient. Additional embodiments include receivers which are located outside of the patient. Examples of receives outside the patient include programmers. Some embodiments of the present subject matter include implantable sensors which are equipped for bi-directional communication. Some of these embodiments employ a transceiver mounted in the implantable sensor device.

The present subject matter provides devices which demonstrate smaller sizes. Devices should be small to reduce tissue damage during implantation. Additionally, devices should be small to reduce the invasive nature of the device to the patient. Applications of the present subject matter include, but are not limited to, devices implanted endovascularly.

Considering the range of applications contemplated by the present subject matter, various design parameters are important. For example, it is important to provide an implantable device which reduces hydrodynamic drag. It is important to provide an implantable device which reduces turbulence. It is important to provide an implantable device which reduces fluid sheer stress. It is important to provide an implantable device which reduces stagnation.

In embodiments implanted in vasculature, an improper design in light of any these phenomena can lead to the creation of an embolus. An embolus, in some applications, can lead to occlusion of the vessel. The present subject matter provides devices which reduce such risks.

The present subject matter additionally addresses the need to provide an implantable device which has mechanical characteristics which reduce tissue damage during implantation. The present subject matter provides a battery having an exterior which is conformable during implantation and in use, in part to address the need to reduce tissue damage during implantation. In some embodiments, an implantable device is adapted to flex in response to a mechanical bias provided by tissues such as vascular tissue. Other benefits of the present subject matter in various embodiments include provision of a conformable shape can which improve patient comfort. A further benefit includes provision of a power source sufficient to satisfy a specified service interval.

FIG. 1 is a cross section of an implantable device including a plurality of flexible battery layers, according to one embodiment of the present subject matter. The implantable device 100 includes one or more flat formable substrates 110. In various embodiments, the one or more flat formable substrates include electrolytic coatings 120. In various embodiments, the electrolytic coatings 120 constitute at least part of an electrochemical cell. Electrochemical cells contemplated by the present subject matter include, but are not limited to, primary batteries and secondary batteries. In various embodiments, the exterior 102 includes a biocompatible flexible coating 130. In various embodiments, the biocompatible flexible coating 130 provides a protective housing. In additional embodiments, the biocompatible flexible coating 130 provides a low profile sleeve. In various embodiments, such a design is able to traverse a circulatory system of the subject's body. Embodiments which are sized for traversal of a circulatory system during implantation are contemplated. Embodiments which are adapted for chronic implantation are additionally contemplated. In various embodiments, the form factor of device 100 depends on the application. For example, embodiments which determine form factor depending on hydrodynamic drag at an implant size are contemplated. Embodiments which determine form factor as a function of turbulence are contemplated. Embodiments which determine form factor as a function of fluid sheer stress are contemplated. Embodiments which determine form factor as a function of reduces stagnation are contemplated. The present subject matter contemplates embodiments in which multiple design criteria are considering during the determination of form factor.

Some embodiments of the present subject matter are adapted for implantation in a body lumen. Some of these embodiments fix the device to tissue. Some embodiments allow the device to free float in the lumen. In some embodiments, the form factor is designed to be nonocclusive. For example, in some embodiments, an implantable medical device is fixed to a stent-like anchor disposed at least partially in vasculature. The applications set forth herein are not intended to be limiting or exhaustive. Form factors are designed to satisfy requirements of applications, including, but not limited to, placement in the body outside vasculature.

The cross section demonstrated in FIG. 1 is taken along a chord of a battery which is circular in the top view. This is one embodiment. The present subject matter extends to embodiments having different shapes, including, but not limited to, cylindrical shapes, prismatic shapes, and other shapes. In various embodiments the flat substrates 110 are substantially planar. In various embodiments, the substrates 110 are formed in other shapes, including, but not limited to, rolls.

According to one embodiment of the present subject matter, the exterior biocompatible flexible coating 130 includes thermoplastic urethane polymer material. There are a number of formulations within this class of polymers which are further outlined the signed U.S. Pat. No. 6,664,335, "Polyurethane Elastomer Article with 'Shape Memory' and Medical Devices Therefrom," filed Nov. 30, 2000, which is commonly assigned and incorporated herein by reference in its entirety. Additional flexible biocompatible coatings may be employed without departing from the scope of the present subject matter.

Figure 2:
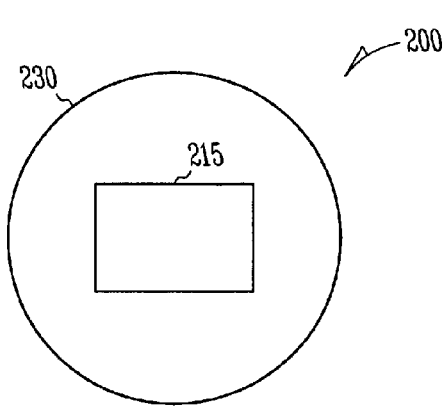
FIG. 2 is a top view of a power source including a conformable housing, according to one embodiment of the present subject matter.

FIG. 2 is a top view of a power source 200 including a conformable housing, according to one embodiment of the present subject matter. The illustration includes a cell 215. The illustration shows a conformable housing 230 enclosing the cell 215, according to various embodiments of the present subject matter. In some embodiments, the cell 215 is rigid. In some embodiments, the cell 215 is flexible. This use of conformable housing 230 improves overall power source 200 flexibility, in various embodiments. Such a configuration, in various embodiments, provides a power source 200 which is compatible with a wider range of applications.

Although the shape of the cell 215 is shown to be prismatic and residing within a substantially circular housing 230, such geometries are only demonstrative and are varied without departing from the scope of the present subject matter. It is noted that other variations may be utilized in order to attain the desired size and energy for the implant application.

Figure 3:
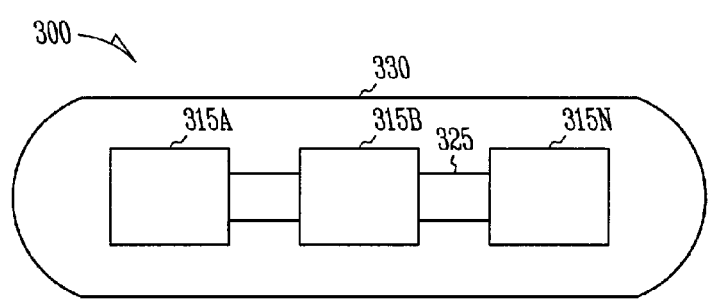
FIG. 3 is a cross sectional illustration of a power source, according to one embodiment of the present subject matter.

FIG. 3 is a cross sectional illustration of a power source, according to one embodiment of the present subject matter. The implantable medical device 300 comprises multiple cells 315A, 315B, . . . , 315N. In some embodiments of the present subject matter, the multiple cells 315A, 315B, . . . , 315N are interconnected to one another. In various embodiments, conductive substrate 325 interconnects the multiple cells 315A, 315B, . . . , 315N. In various embodiments, conductive substrate 325 is composed of multiple parts. In additional embodiments, conductive substrate 325 is a single piece which accommodates multiple cells 315A, 315B, . . . , 315N. In various embodiments, multiple cells 315A, 315B, . . . , 315N and conductive substrate 325 are contained within a conformable housing 330. In some embodiments of the present subject matter, the cells 315A, 315B, . . . , 315N are flexible. In additional embodiments, the cells 315A, 315B, . . . , 315N are rigid. In various embodiments, flexible conductor substrate 325 provides the electrical connection in addition to promoting the flexible nature of the overall device 300. In some embodiments, multiple cells 315A, 315B, . . . , 315N are rigid and are oriented adjacent to one another. In some of these embodiments, the conformable housing 330 accommodates the overall combination.

According to one embodiment the cells 315A, 315B, . . . , 315N comprise two or more cells electrically connected in series. In another embodiment the cells 315A, 315B, . . . , 315N comprise two or more cells electrically connected in parallel. In yet another embodiment cells 315A, 315B, . . . , 315N comprise at least one cell electrically connected in series and at least one cell electrically connected in parallel. In one embodiment the cells 315A, 315B, . . . , 315N comprise at least one primary cell. In another embodiment, the cells 315A, 315B, . . . , 315N comprise at least on secondary cell.

In one embodiment the flexible conductor substrate 325 is formed of a bent conductive wire having a circular cross section. In another embodiment the flexible conductor substrate 325 is stamped out of flat conductive material. The conductive material may be formed of a biocompatible material including, but not limited to: titanium (Ti), platinum (Pt), iridium (Ir), osmium (Os), rhodium (Rh), niobium (Nb), gold (Au), silver (Ag), stainless steel and various combinations. The stamped pattern may then be conformed to a final orientation. Some such acts include, but are not limited to, folding, bending, and/or forming into a three dimensional form to attain the selected final orientation. Other materials and construction methods may be employed without departing from the scope of the present subject matter.

Figure 4:
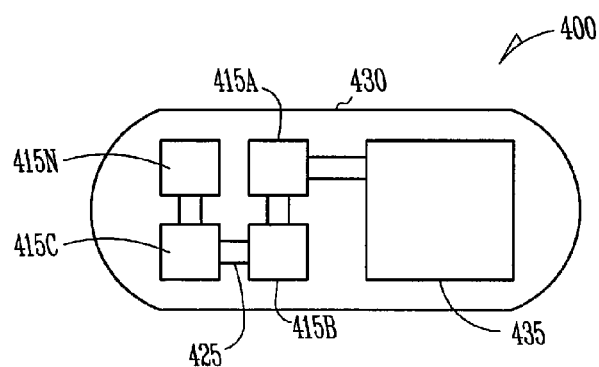
FIG. 4 illustrates an implantable device including a power source interconnected to implantable device subcomponents, according to one embodiment of the present subject matter.

FIG. 4 illustrates an implantable device including a power source interconnected to implantable device subcomponents, according to one embodiment of the present subject matter. In various embodiments, device 400 is an implantable medical device 400. In some of these embodiments, the device is comprised of multiple cells 415A, 415B, . . . , 415N, which are interconnected by flexible conductor substrate 425. In some embodiments, the cells 415A, 415B, . . . , 415N are rigid. In additional embodiment, the cells 415A, 415B, . . . , 415N are flexible.

Additionally, shown are electronics 435. In various embodiments, electronics 435 are connected to the cells 415A, 415B, . . . , 415N via conductor substrate 425. The conformable housing 430 encloses substantially all of the system, in various embodiments. In some embodiments, the conformable housing 430 provides protection. In additional embodiments, the conformable housing 430 provides conformability during implant. In various embodiments, the device 400 provides reduced obstruction of flow through a body lumen.

Although the present subject matter illustrates an embodiment in which electronics and a power source are disposed in a conformable housing 430, other embodiments are possible. For example, some embodiments include a battery having a non-conformable housing and a conformable linkage adapted for connection to other electronics. Some embodiments include a battery having a conformable housing and a conformable linkage. In one example, a conformable battery is non-conformably linked to a non-conformable housing for electronics. A conformable housing, in various embodiments, is that which conforms when a bias is introduced from abutting tissue. Such a bias exists both during implantation and during chronic use. Various embodiments link conformable housings with nonconformable housings using a linkage. Such a linkage, in some embodiments, is hermetic. Other variations of these combinations are contemplated by the present subject matter.

In one embodiment, the electronics 435 include a pressure transducer. A pressure transducer, in various embodiments, is adapted to record pressure data and to communicate pressure data to additional electronics internal to, or external to, the implantable device 400. Various additional embodiments falling within the present scope include other transducers, such as temperature transducers and chemical transducers. Such transducers may be used in differing combinations. Transducers may additionally be used in arrays. Those of skill in the art will appreciate many possible applications of the present subject matter upon reading and understanding the examples set forth herein.

Electronics 435, in various embodiments, include various subcomponents. Some embodiments include subcomponents adapted to communicate energy with devices external to the implantable device 400. In some of these embodiments, the energy is communicated wirelessly. Embodiments within the present subject matter include, but are not limited to, ultrasonic transducers, inductive transducers, and other wireless transducers.

Additional components are included as well. Electronics 435 include, in various embodiments, components for wireless communication of information to devices external to the implantable device. Additionally, in various embodiments, electronics 435 include sensor electronics which communicate data. Some of these embodiments include a pressure transducer. Also, in some embodiments, electronics 435 include stimulation electronics. Medical devices contemplated by the present subject matter include, but are not limited to, defibrillators, cardioverters, pacemakers, neurostimulators, pulse generation devices, and other devices not listed herein expressly. Some embodiments include a processor interconnected to other components to assist other components in communicating with each other. These components are not an exhaustive or exclusive list covering the scope of the present subject matter, and additional components not expressly listed herein additionally fall within the present scope.

Various embodiments incorporate battery chemistries compatible with the present configurations. Embodiments within the present scope include, but are not limited to, at least one of a metal oxide, a metal sulfide, a metal selenide, a metal halide, a metal oxyhalide compound, and corresponding lithiated forms. Some of these embodiments include at least one of manganese, vanadium, silver, molybdenum, tungsten, cobalt, nickel, chromium, and main group compounds such as carbon monofluoride and iodine. Additionally, some embodiments include at least one of carbon, lithium, sodium, potassium, rubidium, cesium, magnesium, calcium, strontium, barium, tin, zinc or silver.

Primary battery chemistry embodiments fall within the present scope. Additionally, secondary battery chemistry embodiments fall within the present scope. In some embodiments a power source of an implantable device includes a plurality of batteries connected in series, parallel or a combination of series and parallel.

Various electrode constructions fall within the present scope. Embodiments compatible with the present subject matter include monolithic electrodes, pelleted electrodes, and other electrodes which have a solid shape. Pelleted electrodes, in various embodiments, include pellets formed from compressed powder, dough or slurry. Some electrode embodiments are formed from a tightly wound ribbon which is wound unto itself without an insulator to separate progressive wraps from one another. Additionally, some embodiment include an electrode onto which is pressed or coated an electronically conductive material. Other electrode configuration embodiments compatible with the present subject matter additionally fall within the present scope.

Additionally, various battery profiles using these electrodes fall within the present scope. Embodiments with the present scope include, but are not limited to, batteries having a cylindrical shape, batteries having a prismatic shape, batteries having a button shape, and batteries having other shapes. In some examples, batteries have shape which is determined as a function of the shape's impact on reducing blood flow. In some examples, batteries have shape which is determined as a function of the shape's impact on reducing tissue damage during implantation.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An apparatus for implantation in a selected lumen of vasculature, comprising:
    a first cell that is prismatic and that includes a first plurality of substantially planar battery electrodes that are arranged in layers;
    a second cell including a second plurality of substantially planar battery electrodes that are arranged in layers;
    a flexible substrate electrically connecting the first cell and the second cell;
    a transducer electrically connected to the first cell via the flexible substrate, the transducer to record medical-related data;
    a wireless transmitter electrically connected to the first cell and to the transducer via the flexible substrate, the wireless transmitter to transmit the medical-related data; and
    a biocompatible flexible housing enclosing the first cell, the second cell, the transducer, the wireless transmitter and the flexible substrate, the biocompatible flexible housing adapted to allow the first cell, the second cell and the transducer to move with respect to one another, the biocompatible flexible housing defining a housing exterior including a form factor shaped as a function of flow stagnation in the selected lumen, the form factor shaped to allow flow in the selected lumen.

2. The apparatus of claim 1, wherein the transducer is a pressure transducer.

3. The apparatus of claim 1, wherein the wireless transmitter is a radio transmitter.

4. The apparatus of claim 1, wherein the wireless transmitter is an ultrasonic transmitter.

5. The apparatus of claim 1, wherein the biocompatible flexible housing include a thermoplastic urethane polymer.

6. The apparatus of claim 5, wherein the biocompatible flexible housing has an elasticity which is less than the elasticity of the vasculature.

7. The apparatus of claim 1, wherein one or more flexible conductors interconnect the first cell and the second cell in parallel.

8. The apparatus of claim 1, wherein one or more flexible conductors interconnect the first cell and the second cell in series.

9. The apparatus of claim 1, wherein the biocompatible flexible housing is elongate, and the first cell, the transducer, and the wireless transmitter are configured along the biocompatible flexible housing in a column orientation.

10. The apparatus of claim 9, wherein the biocompatible flexible housing is substantially cylindrical.

11. The apparatus of claim 1, further comprising a first and second electrode connected to the transducer and sealingly extending through the biocompatible flexible housing, wherein the transducer is adapted to convert power from the first cell to a voltage at the electrodes.

12. The apparatus of claim 11, further comprising neurostimulation electronics adapted to regulate the voltage at the first and second electrodes.

13. The apparatus of claim 1, wherein the first cell includes lithium.

14. An apparatus for implantation in a selected lumen of vasculature, comprising:
    a battery that is prismatic and that includes a first plurality of substantially planar battery electrodes arranged in layers comprising a first cell;
    a second battery including a second plurality of substantially planar battery electrodes arranged in layers comprising a second cell;
    a flexible substrate electrically connecting the first cell and the second cell;
    a transducer electrically connected to the battery via the flexible substrate, the transducer to record medical-related data;
    a wireless transmitter electrically connected to the battery and to the transducer via the flexible substrate, the wireless transmitter to transmit the medical-related data; and
    a biocompatible flexible housing enclosing the battery, the second battery, the transducer, the wireless transmitter and the flexible substrate, the biocompatible flexible housing adapted to allow the first cell, the second cell and the transducer to bend in relation to one another, the biocompatible flexible housing defining a housing exterior including a form factor shaped as a function of flow stagnation in the selected lumen, the form factor shaped to allow flow in the selected lumen.

15. The apparatus of claim 14, wherein the biocompatible flexible housing includes a thermoplastic urethane polymer material.

16. The apparatus of claim 14, wherein the battery includes lithium.

17. The apparatus of claim 14, wherein the battery is flexible and is adapted to conform to a mechanical bias introduced by the vasculature.

18. The apparatus of claim 14, wherein the battery is substantially inflexible.

19. A method for disposing a device at an implant site, comprising:
    measuring fluid flow in a selected lumen;
    determining a form factor of a biocompatible flexible housing as a function of flow stagnation in the selected lumen to reduce stagnation in the selected lumen;
    placing a plurality of battery electrodes into a first cell;
    placing a second plurality of battery electrodes into a second cell;
    interconnecting the first cell, the second cell, a transducer and a wireless transmitter with a flexible substrate, the transducer for recording medical-related data, the wireless transmitter for transmitting the medical-related data; and
    disposing the first cell, the second cell, the transducer, the wireless transmitter and the flexible substrate in a biocompatible flexible housing having the determined form factor; and
    implanting the biocompatible flexible housing at the implant site, with implanting including bending the biocompatible flexible housing to conform to the implant site.

20. The method of claim 19, further comprising disposing a plurality of batteries in the biocompatible flexible housing.

21. The method of claim 19, further comprising stimulating the implant site with the transducer.

22. The method of claim 19, further comprising recording pressure data with the transducer and broadcasting the pressure data using the wireless transmitter.

* * * * *